(12) United States Patent
Hsu et al.

(10) Patent No.: US 11,944,486 B2
(45) Date of Patent: Apr. 2, 2024

(54) ANALYSIS METHOD FOR BREAST IMAGE AND ELECTRONIC APPARATUS USING THE SAME

(71) Applicant: TAIHAO MEDICAL INC., Taipei (TW)

(72) Inventors: Jen-Feng Hsu, Taoyuan (TW); Hong-Hao Chen, Hsinchu (TW); Rong-Tai Chen, Taichung (TW); Hsin-Hung Lai, Taipei (TW); Wei-Han Teng, Taipei (TW)

(73) Assignee: TAIHAO MEDICAL INC., Taipei (TW)

(*) Notice: Subject to any disclaimer, the term of this patent is extended or adjusted under 35 U.S.C. 154(b) by 186 days.

(21) Appl. No.: 17/378,775

(22) Filed: Jul. 19, 2021

(65) Prior Publication Data

US 2021/0338194 A1    Nov. 4, 2021

Related U.S. Application Data

(63) Continuation-in-part of application No. 15/622,077, filed on Jun. 14, 2017, now abandoned.

(30) Foreign Application Priority Data

Jun. 27, 2016   (TW) ................................ 105120124

(51) Int. Cl.
  *A61B 8/08*     (2006.01)
  *G06T 7/11*     (2017.01)
  (Continued)

(52) U.S. Cl.
  CPC ............ *A61B 8/0825* (2013.01); *A61B 8/085* (2013.01); *A61B 8/483* (2013.01); *G06T 7/11* (2017.01);
  (Continued)

(58) Field of Classification Search
  CPC ..... A61B 8/0825; A61B 8/065; A61B 8/0833; A61B 8/0858
  See application file for complete search history.

(56) References Cited

U.S. PATENT DOCUMENTS

| 2009/0149750 A1* | 6/2009 | Matsumura ......... A61B 5/0053 600/438 |
| 2018/0000453 A1* | 1/2018 | Hunter ................ G06F 3/04883 |

(Continued)

FOREIGN PATENT DOCUMENTS

| CN | 104546013 A | * | 4/2015 | ........... A61B 8/0825 |
| CN | 104657984 A | * | 5/2015 | ............... A61B 8/00 |

*Primary Examiner* — Keith M Raymond
*Assistant Examiner* — Johnathan Maynard
(74) *Attorney, Agent, or Firm* — JCIPRNET

(57) ABSTRACT

An analysis method and an electronic apparatus for breast image are provided. The method includes the following steps. One or more breast ultrasound images are obtained. The breast ultrasound images are used for forming a three-dimensional (3D) breast model. A volume of interest (VOI) in the breast ultrasound image is obtained by applying a detection model on the 3D breast model. The VOI is compared with a tissue segmentation result. The VOI is determined as a false positive according to a compared result between the VOI and the tissue segmentation result. The compared result includes that the VOI is located at a glandular tissue based on the tissue segmentation result. In response to the VOI being located in the glandular tissue of the tissue segmentation result, the VOI is compared with the lactiferous duct in the 3D breast model.

20 Claims, 13 Drawing Sheets

(51) Int. Cl.
  *G06T 7/149*      (2017.01)
  *G06T 17/00*      (2006.01)
  *G06V 10/143*     (2022.01)
  *G06V 10/25*      (2022.01)
  *G06V 10/50*      (2022.01)
  *G06V 10/75*      (2022.01)

(52) U.S. Cl.
  CPC .............. *G06T 7/149* (2017.01); *G06T 17/00* (2013.01); *G06V 10/143* (2022.01); *G06V 10/25* (2022.01); *G06V 10/50* (2022.01); *G06V 10/75* (2022.01); *G06T 2207/10132* (2013.01); *G06T 2207/20081* (2013.01); *G06T 2207/30068* (2013.01)

(56)             References Cited

U.S. PATENT DOCUMENTS

| | | | |
|---|---|---|---|
| 2018/0109698 A1* | 4/2018  | Ramsay   | G06T 11/001 |
| 2019/0053789 A1* | 2/2019  | Malik    | G06F 18/2411 |
| 2020/0069275 A1* | 3/2020  | Stavros  | G06T 7/97 |
| 2020/0345292 A1* | 11/2020 | Stavros  | A61B 8/0825 |
| 2022/0036545 A1* | 2/2022  | St. Pierre | A61B 8/5223 |

* cited by examiner (5a)

(5b)

(5c)

(5d)

| Determining that the VOI is located in glandular tissue of the tissue segmentation result | ~ S1210 |

↓

| In response to the VOI being located in the glandular tissue, comparing the VOI with the lactiferous duct in the 3D breast model | ~ S1230 |

ANALYSIS METHOD FOR BREAST IMAGE AND ELECTRONIC APPARATUS USING THE SAME

CROSS REFERENCE TO RELATED APPLICATION

This application is a continuation-in-part application of and claims the priority benefit of U.S. application Ser. No. 15/622,077, filed on Jun. 14, 2017, now pending, which claims the priority benefit of Taiwan application serial no. 105120124, filed on Jun. 27, 2016. The entirety of each of the above-mentioned patent applications is hereby incorporated by reference herein and made a part of specification.

BACKGROUND OF THE INVENTION

1. Field of the Invention

The invention relates to an analysis method and an electronic apparatus using the same, and more particularly, to an analysis method for analyzing breast image and an electronic apparatus using the same.

2. Description of Related Art

Mammary carcinoma is a common female malignant tumor, and the main symptom includes breast tumors, abnormal secretions, or shape variation, etc. Screening an aberrant symptom for breast in advance can facilitate in treating the tumor earlier so that deterioration or proliferation of cancer cells can be reduced. Screening methods, such as clinical or self breast detection, biopsy, mammography, ultrasound or magnetic resonance imaging and the like, have been widely used in clinical practice or have become important issues in academic researches.

Traditionally, after a breast image is obtained, medical personnel then examines and verifies whether an aberrant part is included in the breast image. If the aberrant part is found, a different inspection method is used to confirm whether the aberrant part is the malignant tumor. However, when there are a massive number of the breast images, it is very time-consuming and ineffective for medical personnel to examine whether the aberrant part is included in the breast images one by one. On the other hand, mistakes can often be made if the aberrant part in the breast image is filtered only by the human eye.

Accordingly, developing an analysis method and an electronic apparatus using the same to effectively detect, analyze and acquire the aberrant part in the breast image is still one of the major subjects for person skilled in the art.

SUMMARY OF THE INVENTION

The invention is directed to an analysis method for breast image and an electronic apparatus using the same, which can be used to detect, analyze and obtain an aberrant part in the breast image.

An embodiment of the invention provides an analysis method for breast image, which includes the following steps. One or more breast ultrasound images are obtained. The breast ultrasound images are used for forming a three-dimensional (3D) breast model. A volume of interest (VOI) is obtained in the breast ultrasound image by applying a detection model on the 3D breast model. The detection model is trained by a machine learning algorithm. The VOI is compared with a tissue segmentation result. The tissue segmentation result includes multiple tissues in the 3D breast model. The VOI is determined as a false positive according to the compared result between the VOI and the tissue segmentation result. The compared result includes that the VOI is located at a glandular tissue based on the tissue segmentation result. The step of comparing the VOI with the tissue segmentation result further includes the following steps. The fact that the VOI is located in the glandular tissue of the tissue segmentation result is determined. In response to the VOI being located in the glandular tissue, the VOI is compared with the lactiferous duct in the 3D breast model.

An embodiment of the invention provides an electronic apparatus adapted for analyzing breast image. The electronic apparatus includes a memory and a processor. The memory is configured to store program code(s), and the processor coupled to the memory is configured to access and execute the program code stored by the memory. The processor is configured for obtaining one or more breast ultrasound images, obtaining a VOI in the breast ultrasound image by applying a detection model on the 3D breast model, comparing the VOI with a tissue segmentation result, and determining the VOI as a false positive according to a compared result between the VOI and the tissue segmentation result. The breast ultrasound image is used for forming a 3D breast model. The detection model is trained by a machine learning algorithm. The tissue segmentation result includes a plurality of tissues in the 3D breast model. The compared result includes the VOI is located at a glandular tissue based on the tissue segmentation result. The processor is further configured for determining that the VOI is located in glandular tissue of the tissue segmentation result, and comparing the VOI with the lactiferous duct in the 3D breast model in response to the VOI being located in the glandular tissue.

Based on the above, according to the analysis method for breast image and the electronic apparatus using the same as provided in the embodiments of the invention, the region of interest (ROI) or VOI including the aberrant region is obtained from the breast (ultrasound) image by applying the detection model based on the rectangular features of the breast image such that the aberrant region can be acquired from the region of interest. With respect to the aberrant region, the feature parameters can be further extracted for the property analysis, and whether multiple aberrant regions belong to the same tumor can also be determined and correspondingly displayed. As a result, the analysis method and the electronic apparatus using the same can be used to identify the aberrant region with the aberrant symptom while providing the related property analysis. On the other hand, the analysis can be completed rapidly, promptly and effectively even in the case of dealing with a massive number of breast ultrasound images.

To make the above features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
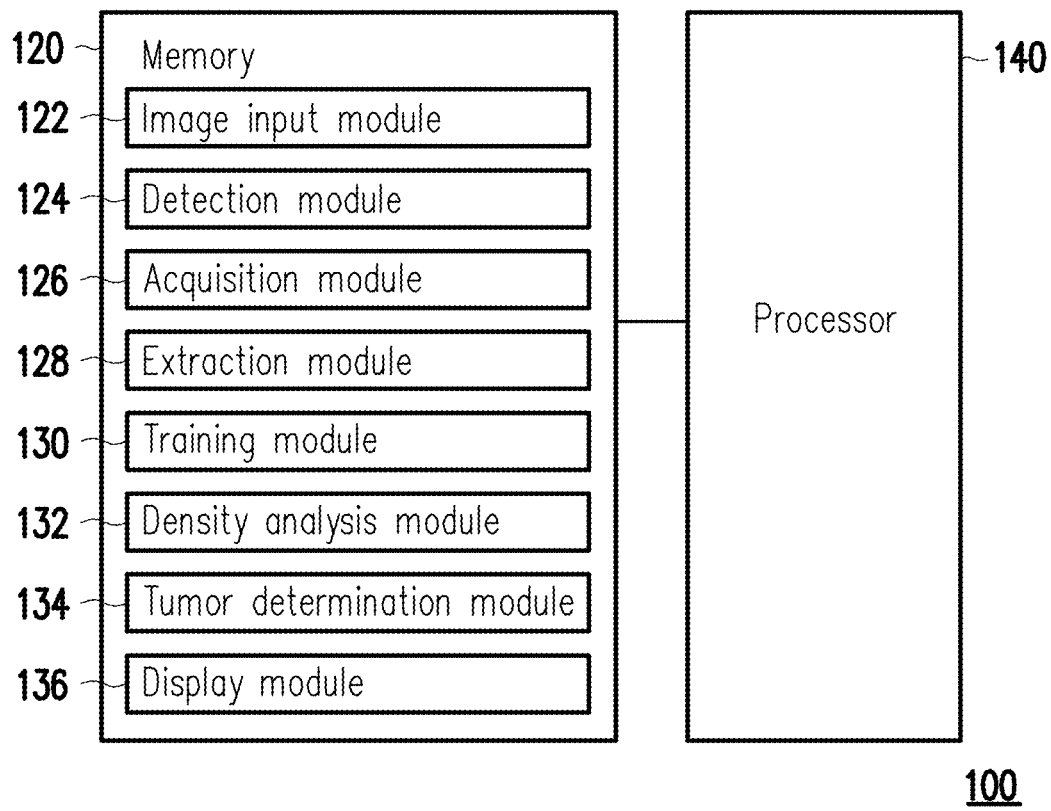
FIG. 1 is a block diagram illustrating an electronic apparatus according to an embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

Some embodiments of the invention are described in details below by reference with the accompanying drawings, and as for reference numbers cited in the following description, the same reference numbers in difference drawings are referring to the same or like parts. The embodiments are merely a part of the invention rather than disclosing all possible embodiments of the invention. More specifically, these embodiments are simply examples of devices and methods recited in claims of the invention.

In the analysis method for breast image and the electronic apparatus using the same as proposed in the embodiments of the invention, first of all, a region of interest (ROI) including an aberrant region in a breast image is obtained by applying a detection model based on a plurality of rectangular features of the breast image. The aberrant region refers to a region showing the aberrant symptom in the breast image. More specifically, the region showing the aberrant symptom may be a tumor or a symptom, and a trained detection model can assist in detecting and identifying the aberrant region.

The analysis method and the electronic apparatus using the same can also acquire the aberrant region from the region of interest precisely and extract related feature parameters for a property analysis, so as to improve accuracy in subsequent diagnosis for breast. In addition, the analysis method and the electronic apparatus using the same are also capable of calculating and providing an overall breast density as a diagnostic reference from multiple breast images.

FIG. 1 is a block diagram illustrating an electronic apparatus according to an embodiment of the invention. With reference to FIG. 1, an electronic apparatus 100 at least includes a memory 120 and a processor 140, where the processor 140 is coupled to the memory 120. However, the invention is not limited to the above. In an embodiment of the invention, the electronic apparatus 100 may be a server, a smart mobile device, a desktop computer, a notebook computer, a work station, a personal digital assistant (PDA) or the like, but the invention is not limited thereto.

In the embodiment described above, the electronic apparatus 100 is further connected to an ultrasound device such as an ultrasound scanning apparatus, a handheld ultrasound scanner, an automated breast ultrasound system (ABUS) or a magnetic tracker ultrasound scanning system. However, in other embodiments of the invention, the electronic apparatus 100 is directed implemented in from of the ultrasound scanning apparatus, the handheld ultrasound scanner, the automated breast ultrasound system or the magnetic tracker ultrasound scanning system, for example. In other words, the functions of computer aided detection (CADe) and/or computer aided diagnosis (CADx) provided in the present invention may be integrated in a hardware such as the ultrasound scanning apparatus, the handheld ultrasound scanner, the automated breast ultrasound system or the magnetic tracker ultrasound scanning system directly.

In an embodiment of the invention, the memory 120 may be a fixed or a movable device in any form, including a random access memory (RAM), a read-only memory (ROM), a flash memory, or similar devices or a combination of the aforementioned devices. In the present embodiment, the memory 120 stores multiple modules and/or one or more program codes accessible and executable by the processor 140. The modules include an image input module 122, a detection module 124, an acquisition module 126, an extraction module 128, a training module 130, a density analysis module 132, a tumor determination module 134, a display module 136, etc. The functions and operations of the modules are recorded in one or more program codes. On the other hand, the memory 120 may also be used to store data related to the breast image, the detection model, parameters, etc., but the invention is not limited thereto.

It should be noted that, the memory 120 described in the embodiment above is not limited only to be one single memory device. That is to say, each of the modules may also be separately stored in two or more than two memory devices of the same or different types. In other embodiments of the invention, the modules may also be separately implemented by using a specific circuit structure.

In an embodiment of the invention, the processor 140 is implemented by, for example, a programmable unit such as a central processing unit (CPU), a digital signal processing (DSP) chip, a field programmable gate array (FPGA), a microprocessor, a micro controller, etc., but the invention is not limited thereto. The processor 140 may also be implemented by an independent electronic apparatus or an integrated circuit (IC).

In an embodiment of the invention, the electronic apparatus 100 further includes devices like an input/output interface (not illustrated), a communication interface (not illustrated), etc., but the invention is not limited thereto. Specifically, the input/output interface includes devices for outputting or inputting messages and data, such as a display, a speaker, a keyboard, a mouse, a touch panel, etc. On the other hand, the communication interface supports various communication standards and wireless communication standards so that the electronic apparatus 100 can connect to the other devices.

The analysis method for breast image provided by the embodiments of the invention can be realized by the electronic apparatus 100 illustrated in FIG. 1. Said analysis method is described in details below by various embodiments provided with reference to the electronic apparatus 100 illustrated in FIG. 1. It should be noted that, the analysis method for breast image is not limited only to be realized by the electronic apparatus 100, and instead, the analysis method may also be realized by other electronic apparatuses or systems with the corresponding capability.

Figure 2:
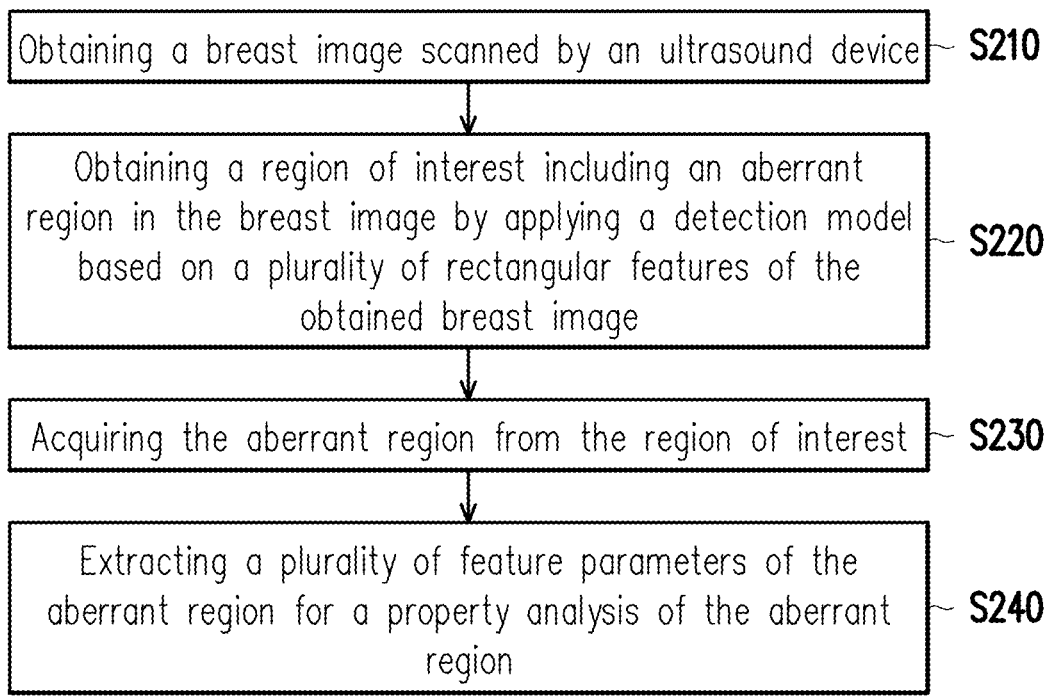
FIG. 2 is a flowchart illustrating an analysis method for breast image according to an embodiment of the invention.

FIG. 2 is a flowchart illustrating an analysis method for breast image according to an embodiment of the invention. With reference to FIG. 1 and FIG. 2, the image input module 122 first obtains a breast image scanned by an ultrasound device (step S210).

In an embodiment of the invention, the breast image, which is also called as the breast ultrasound image, is an image obtained by scanning a breast part of the subject with the ultrasound scanning apparatus, the handheld ultrasound scanner, the automated breast ultrasound system or the magnetic tracker ultrasound scanning system. For example, the image input module 122 receives the breast image directly from the ultrasound scanning apparatus, the handheld ultrasound scanner, the automated breast ultrasound system or the magnetic tracker ultrasound scanning system, but the invention is not limited thereto. In another embodiment of the invention, for example, the electronic apparatus 100 stores the obtained breast image in the memory 120, so the image input module 122 can then read the breast image from the memory 120 for analysis.

With reference to FIG. 1 and FIG. 2, in the present embodiment of the invention, after the breast image is obtained by the image input module 122, the detection module 124 obtains a region of interest including an aberrant region in the breast image by applying a detection mode based on a plurality of rectangular features of the obtained breast image (step S220).

One of the missions assigned to the detection module 124 is to detect and obtain the region of interest including the aberrant region in the breast image. In general, if there is any tumor or mass in the breast part, usually, a shaded region also correspondingly appears in the breast image obtained by scanning with the ultrasound wave. Therefore, in the present embodiment, the detection module 124 can determine whether there is an abnormal shaded region in the breast image by applying the detection model based on the rectangular features of the breast image. If so, the detection module 124 treats the shaded region as the aberrant region, and obtains the region of interest including the aberrant region. It should be noted that, the rectangular features are Haar-like features.

Figure 3:
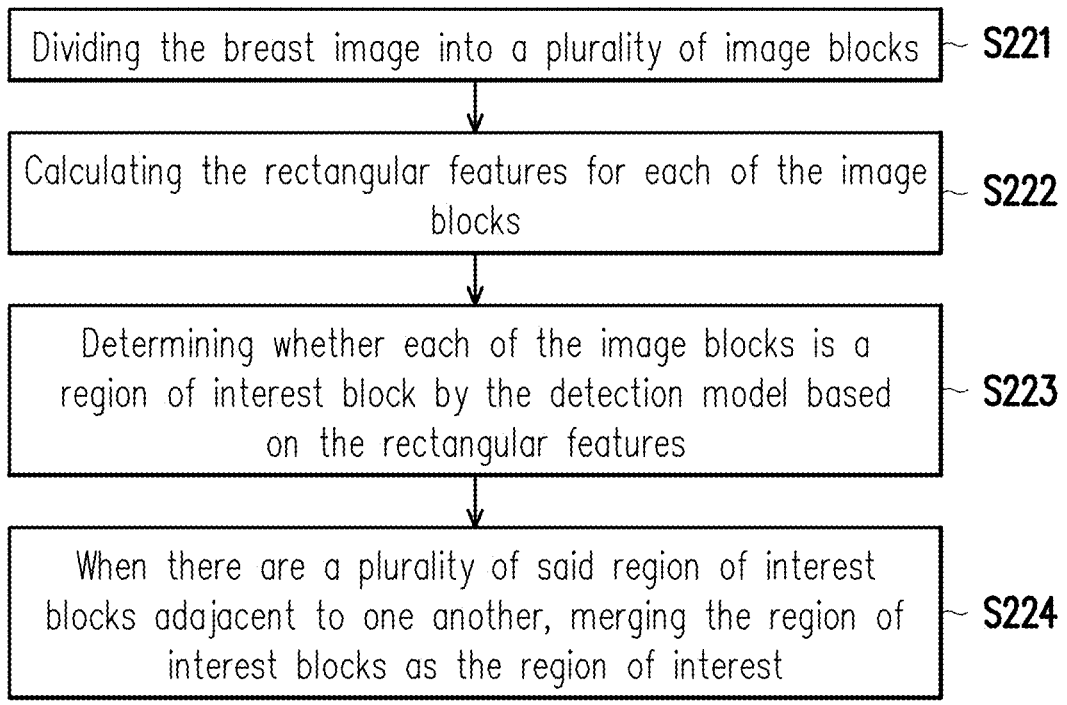
FIG. 3 illustrates a flowchart for obtaining a region of interest according to an embodiment of the invention.

FIG. 3 illustrates a flowchart for obtaining a region of interest according to an embodiment of the invention. With reference to FIG. 1, FIG. 2 and FIG. 3, the detection module 124 divides the breast image into a plurality of image blocks (step S221). A dimension of the image block is, for example, 11*11, 12*12 or 15*20 (pixel). However, the invention is not limited to the above, and the dimension of the image block may be changed depending on actual operational requirements. Next, the detection module 124 calculates the rectangular features for each of the image blocks according to a common rectangular feature template (step S222). In general, the rectangular feature template has an edge feature, a linear feature, a centered-around feature, a diagonal feature and the like.

Next, the detection module 124 determines whether each of the image blocks is a region of interest block by the detection model based on the rectangular features (step S223). More specifically, in an embodiment of the invention, the detection model is used to identify whether at least part of the shaded region caused by the aberrant symptom is included for each of the image blocks, and is trained using the breast images having tumor or mass and the breast images not having tumor or mass. In other words, before the region of interest can be obtained by applying the detection model, a related training must be completed with training breast images.

In an embodiment of the invention, the image input module 122 obtains a plurality of training breast images scanned by the ultrasound device. Then, after calculating the rectangular features for each of the training image blocks, the training module 130 trains a classifier as the detection model based on training image blocks of each of the training breast images. The training breast images are, for example, training breast images having tumor or mass and the training breast images not having tumor or mass, and the classifier is, for example, a binary classifier, such as a support vector machine (SVM), an adaptive boosting (Adaboost) classifier, etc., but the invention is not limited to the above.

Figure 4:
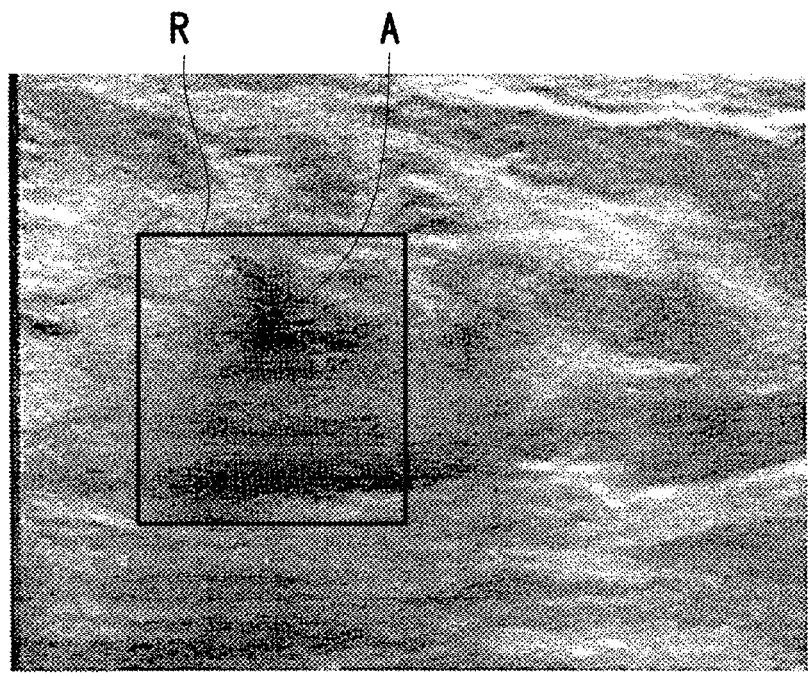
FIG. 4 is a schematic diagram illustrating a region of interest and an aberrant region according to an embodiment of the invention.

With reference to FIG. 1, FIG. 2 and FIG. 3, after determining whether each of the image blocks is the region of interest block, when there are a plurality of said region of interest blocks adjacent to one another, the detection module 124 merges the region of interest blocks as the region of interest (step S224). Specifically, each of the region of interest blocks includes part of the shaded region caused by the aberrant symptom, and thus the detection module 124 can merge the region of interest blocks adjacent to one another as the region of interest having the entire aberrant region. FIG. 4 is a schematic diagram illustrating a region of interest and an aberrant region according to an embodiment of the invention. With reference to FIG. 4, in the breast image, a region of interest R includes an aberrant region A.

In other embodiments of the invention, if there is only one region of interest block, the detection module 124 then treats that region of interest block as the region of interest, for example. On the other hand, the breast image may also include a plurality of said region of interest. In other words, the breast image includes multiple groups of the adjacent region of interest blocks.

In an embodiment of the invention, the detection module 124 is, for example, implemented by a computer aided detection (CADe) module, but the invention is not limited thereto.

It should be noted that, while the ultrasound device is used for scanning, in addition to tumor or mass, ribs or other factors may also cause the shaded region in the breast image. In other words, even though the detection module 124 can obtain the region of interest including the aberrant region by applying the rectangular features of the breast image and the detection model, a false detection may still occur owing to ribs or other factors.

In an embodiment of the invention, the detection module 124 further identifies whether the region of interest is the false detection based on a muscle line. In general, a muscle tissue (e.g., pectoralis major) is also included between the breast part, ribs and intercostal of the subject. In other words, said muscle tissue may be used to determine whether the region of interest is located at the breast part, so as to further identify whether the region of interest is the shaded region caused by ribs or other factors.

Figure 5:
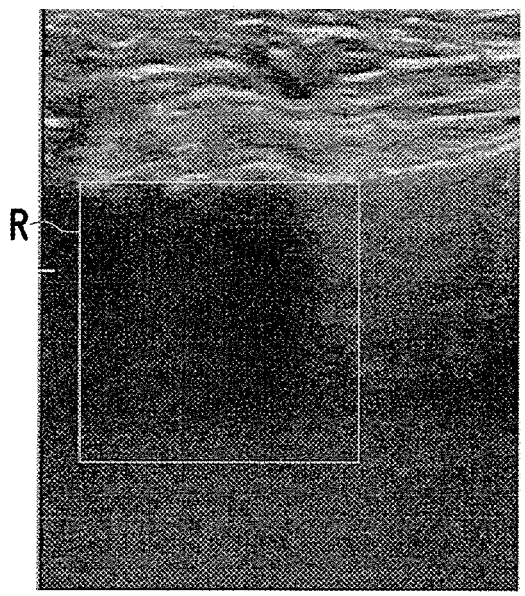
FIG. 5 illustrates a schematic diagram for comparing a muscle line and a region of interest according to an embodiment of the invention.
Figure 5:
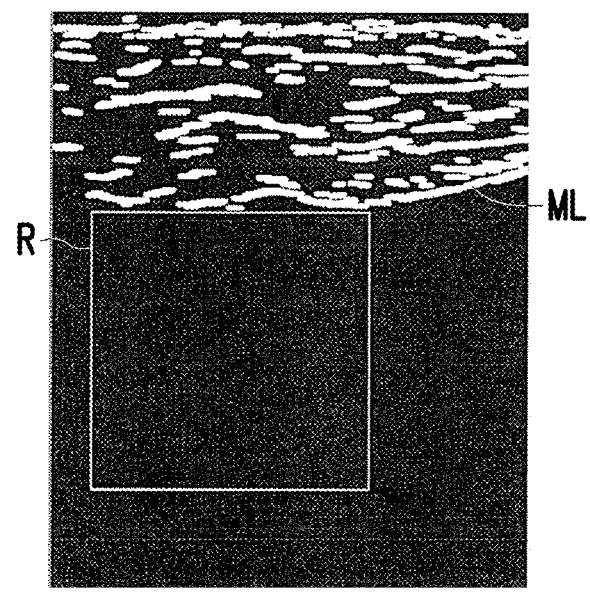
Figure 5:
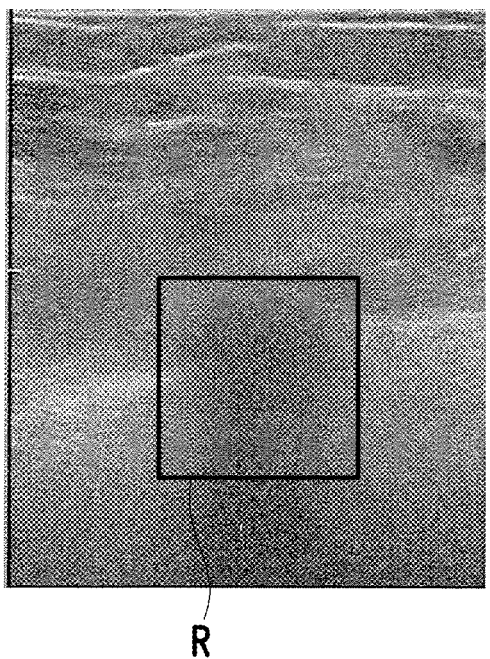
Figure 5:
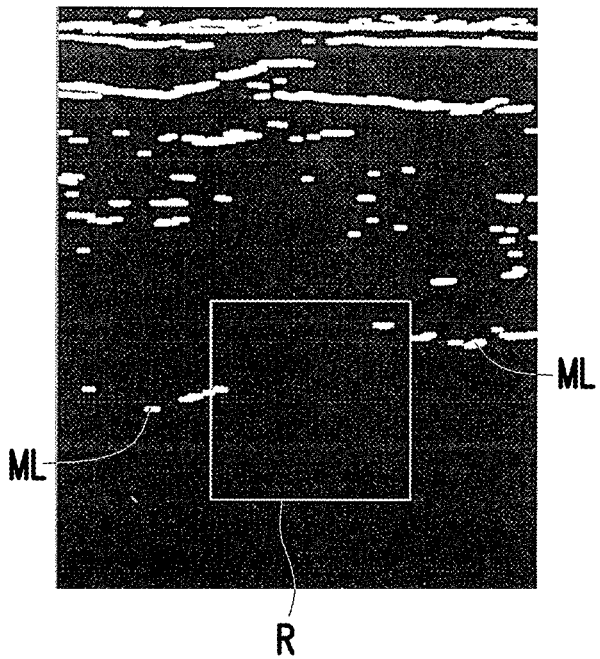

FIG. 5 illustrates a schematic diagram for comparing a muscle line and a region of interest according to an embodiment of the invention. With reference to FIG. 5, the detection module 124 executes an edge detection respectively on a breast image 5a and a breast image 5c followed by enhancing and processing detected edge parts by a mathematical morphology, so as to identify and obtain a muscle line ML as shown in an image 5b and an image 5d. After obtaining the muscle line ML, the detection module 124 compares positions of the muscle line ML and the region of interest R in the images 5b and 5d to determine whether to further acquire the aberrant region from the region of interest R or not.

For instance, the region of interest R in the image 5b located below the muscle line ML indicates that this region of interest R is not located at the breast part. In this case, the subsequent analysis is not performed for the region of interest R of the image 5a. On the other hand, the region of interest R in the image 5d having only a small part protruding above the muscle line ML indicates that this region of interest R is highly possible the shaded region caused by ribs. In this case, the subsequent analysis is not performed for the region of interest R of the image 5c either.

With reference to FIG. 1 and FIG. 2, in the present embodiment of the invention, after obtaining the region of interest including the aberrant region, the acquisition module 126 acquires the aberrant region from the region of interest (step S230). Specifically, the detection module 124 only detects and obtains the region of interest in the breast image, whereas the acquisition module 126 is responsible for executing an image matting (or known as an image alpha analysis) to obtain the aberrant region for the subsequent analysis and diagnosis.

Figure 6:
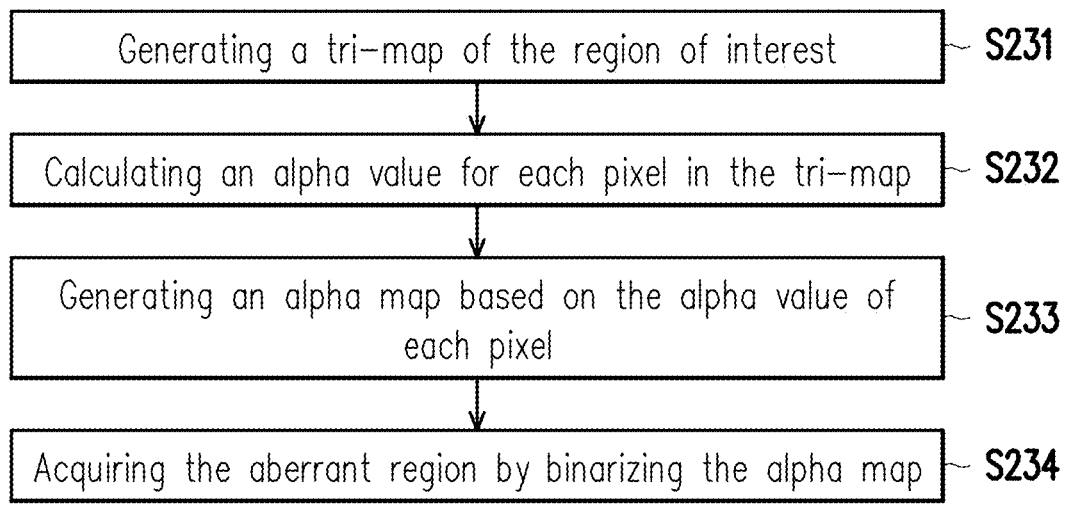
FIG. 6 illustrates a flowchart for acquiring an aberrant region according to an embodiment of the invention.
Figure 7:
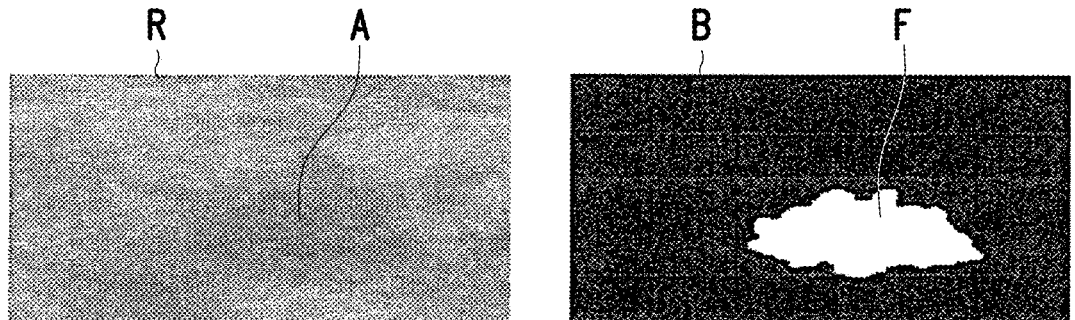
FIG. 7 illustrates a schematic diagram for acquiring an aberrant region according to an embodiment of the invention.
Figure 7:
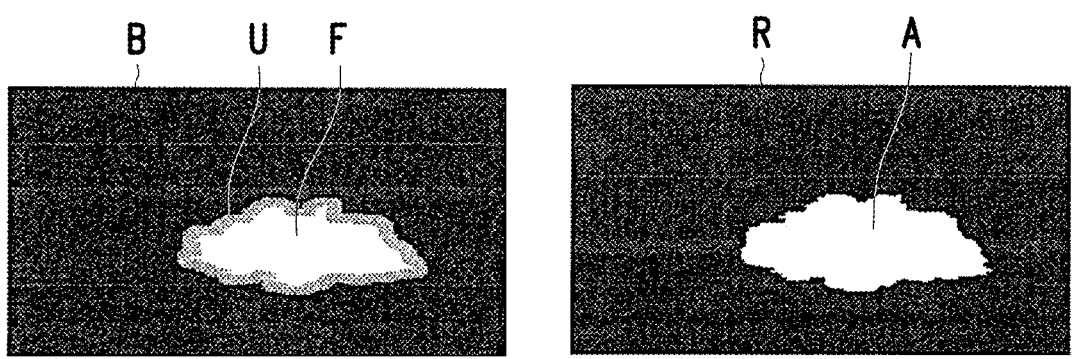

FIG. 6 illustrates a flowchart for acquiring an aberrant region according to an embodiment of the invention. FIG. 7 illustrates a schematic diagram for acquiring an aberrant region according to an embodiment of the invention. With reference to FIG. 1, FIG. 2, FIG. 6 and FIG. 7, the detection module 126 generates a tri-map of the region of interest (step S231). Specifically, in the present embodiment, after the region of interest R of the breast image 7a is obtained, the detection module 126 pre-divides the image by, for example, methods including Level Set, Region growing, etc., so as to generate a frontground image F and a background image B shown in the image 7b and in the image 7b.

In the embodiment described above, the frontground image F of the image 7b mainly corresponds to the aberrant region A of the breast image 7a instead of providing an accurate correspondence relation. After obtaining the frontground image F and the background image B, the acquisition module 126 further places an unknown region U between the frontground image F and the background image B through dilation and erosion to generate a tri-map 7c.

In the present embodiment, after generating the tri-map 7c, the acquisition module 126 calculates an alpha value for each pixel in the tri-map 7c (step S232). Specifically, the acquisition module 126 acquires the aberrant region based on the tri-map 7c. Herein, the acquisition module 126 adopts image division methods such as Closed-form Solution and Poisson Matting to determine an image type to which each pixel in the unknown region U belongs based on the frontground image F and the background image B being given.

In general, in the tri-map 7c composed of the frontground image F and the background image B, each pixel may be expressed by one linear combination below.

$$I_i = \alpha_i F_i + (1-\alpha_i) B_i$$

Herein, $\alpha_i$ is the alpha value of an $i^{th}$ pixel, or a proposition of the $i^{th}$ pixel occupied by the frontground image F and the background image B. After calculating the alpha value for each pixel in the unknown region U or the tri-map, the acquisition module 126 further generates an alpha map based on the alpha value of each pixel (step S233). The alpha map is a transparency diagram including the alpha value of each pixel, and a numerical range of each pixel is within a range from 0 to 255. Lastly, the acquisition module 126 acquires the aberrant region from an image 7d generated by binarizing the alpha map (step S234). The images 7b and 7d are edge-enhanced images, and a method for binarizing includes, for example, Otsu's Thresholding or Balanced Histogram Thresholding, but the invention is not limited thereto.

With reference to FIG. 1 and FIG. 2, in an embodiment of the invention, after acquiring the aberrant region, the extraction module 128 extracts a plurality of feature parameters of the aberrant region for a property analysis of the aberrant region (step S240). Specifically, the extraction module 128 extracts of an intensity feature, a texture feature and a morphology feature of the aberrant region to be the feature parameters as the foundation for the subsequent property analysis or diagnosis.

For instance, in an embodiment of the invention, the feature parameters of the aberrant region are further inputted to a computer aided diagnosis (CADx) module for the property analysis, but the invention is not limited thereto. The computer aided diagnosis module is, for example, executed by the processor 140 or other devices (systems), and has an aided diagnosis model underwent said training. With the aided diagnosis model of the computer aided diagnosis module, analysis data related to the aberrant region (e.g., benign lesion or malignant lesion, lesion condition) can be obtained and provided to medical personnel as diagnostic reference data.

It should be noted that, in the process of scanning the breast part by the ultrasound device, it is usually required to scan the breast part in multiple directions in order to obtain multiple of said breast images. In an embodiment of the invention, the analysis method is used to separately analyze each of the breast image, and obtain the aberrant region and the feature parameters one by one from each of the breast image.

In another embodiment of the invention, the analysis method and the electronic apparatus 100 using the same may further obtain a breast density of the breast part as another feature parameter for analysis.

Figure 8:
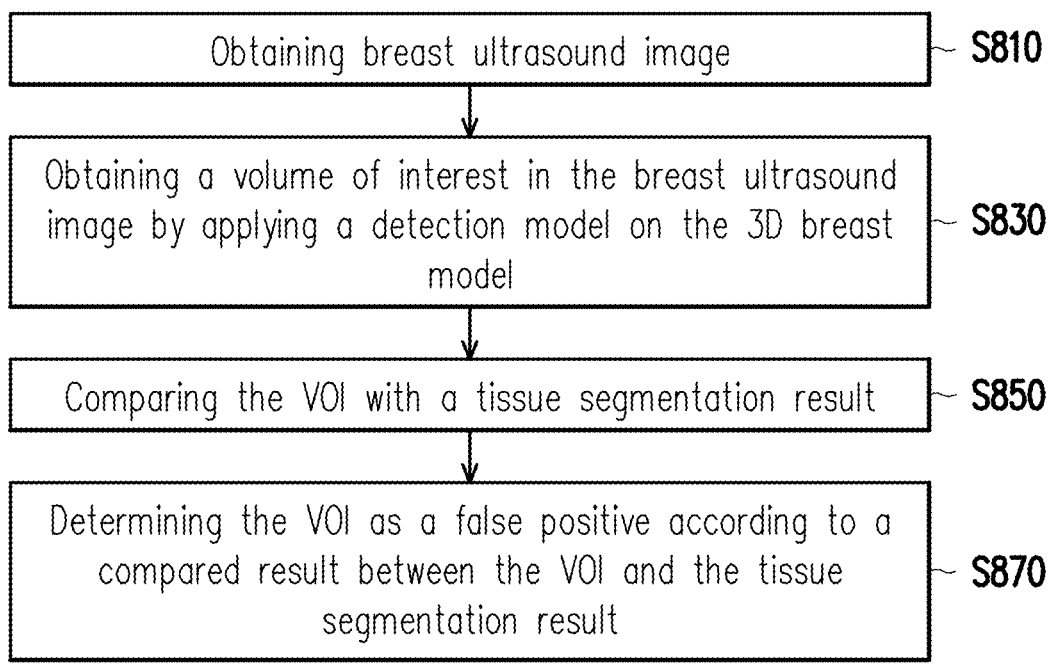
FIG. 8 is a flowchart illustrating an analysis method for breast image according to an embodiment of the invention.

FIG. 8 is a flowchart illustrating an analysis method for breast image according to an embodiment of the invention. With reference to FIG. 1 and FIG. 8, the image input module 122 obtains one or more breast ultrasound images (step S810). In an embodiment of the invention, one or more continuous breast ultrasound images are obtained by the ultrasound-related scanner. These breast ultrasound images may correspond to multiple directions relative to a breast. The processor 140 may further establish a three-dimensional (3D) breast model based on the continuous breast images and their relative locations. In other words, these breast ultrasound images correspond to multiple section views of the breast. The combination of these section views may form a 3D breast model. In some embodiments, the 3D breast model may be obtained from a 3D automated breast ultrasound scanner directly.

The detection module 124 obtains one or more volumes of interest (VOIs) in the breast ultrasound image by applying a detection model on the 3D breast model (step S830). Specifically, the detection model is trained by a machine learning algorithm. The machine learning algorithm may include a convolutional neural network (CNN), a recurrent neural network (RNN), a multi-layer perceptron (MLP), a support vector machine (SVM), a decision tree, or other algorithms. The machine learning algorithm analyzes training samples to obtain a relationship therein, to predict unknown data through the relationship. The detection model is namely a machine learning model constructed after learning, and thereby inference is performed on the to-be-evaluated data. As mentioned before, the detection model is determined based on rectangular features or other image features based on the implemented algorithm. In one embodiment, the detection model is used for determining one or more areas/regions/volumes in the 3D breast model are suspicious areas.

A suspicious area may be a shaded region in the breast ultrasound image. However, a suspicious area may be an artifact or a lesion. The detection module 124 would determine the suspicious area as a VOI and further determine whether the VOI belongs to false positive or true positive. The VOI belonging to the false positive would be removed from the suspicious areas.

Figure 9B:
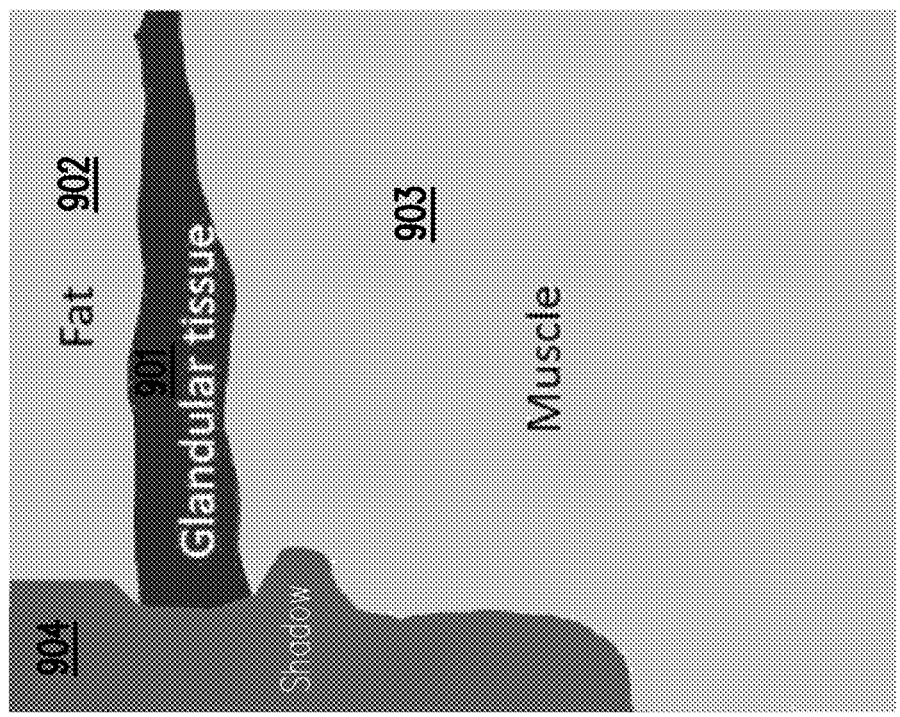
FIG. 9B is a schematic diagram illustrating a tissue segmentation result of FIG. 9A according to an embodiment of the invention.
Figure 9A:
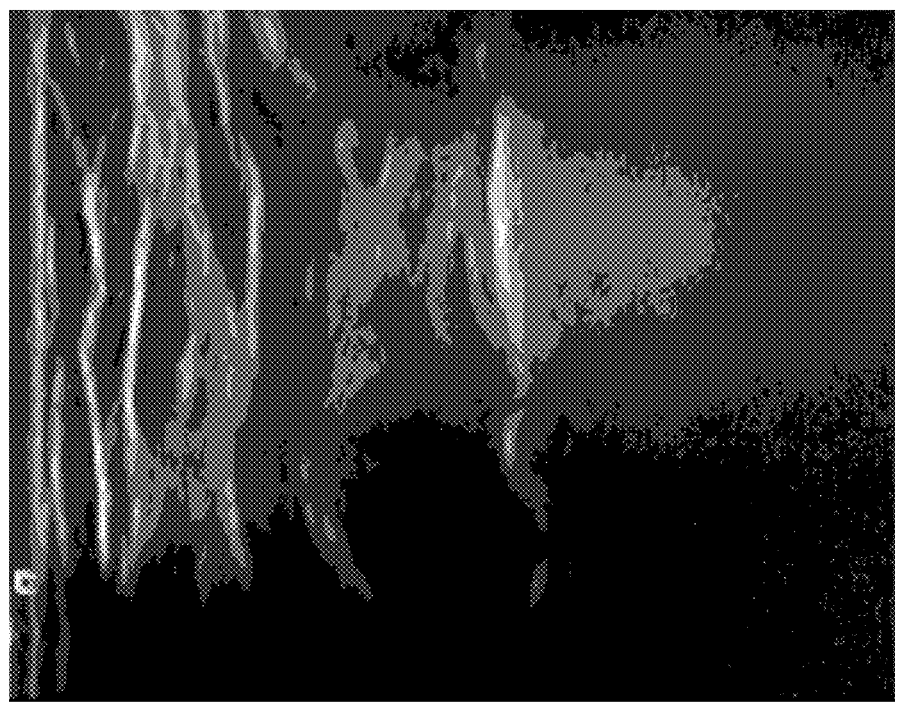
FIG. 9A is an example illustrating a breast ultrasound image according to an embodiment of the invention.

The detection module 124 compares the VOI with a tissue segmentation result (step S850). Specifically, the tissue segmentation result comprises multiple tissues in the 3D breast model. For example, FIG. 9A is an example illustrating a breast ultrasound image according to an embodiment of the invention, and FIG. 9B is a schematic diagram illustrating a tissue segmentation result of FIG. 9A according to an embodiment of the invention. Referring to FIGS. 9A and 9B, the detection module 124 uses a tissue classifier trained by a machine learning algorithm as mentioned above to segment the breast ultrasound image into multiple tissues. The tissues may be glandular tissue 901, fat 902, and muscle 903. Furthermore, if the probe or conductor of the scanner is not enough close to the breast, the distribution of the liquid couplant on the breast is not uniform, or the region is located below the nipple, one or more shadows 904 may be shown on the breast ultrasound image.

Figure 10A:
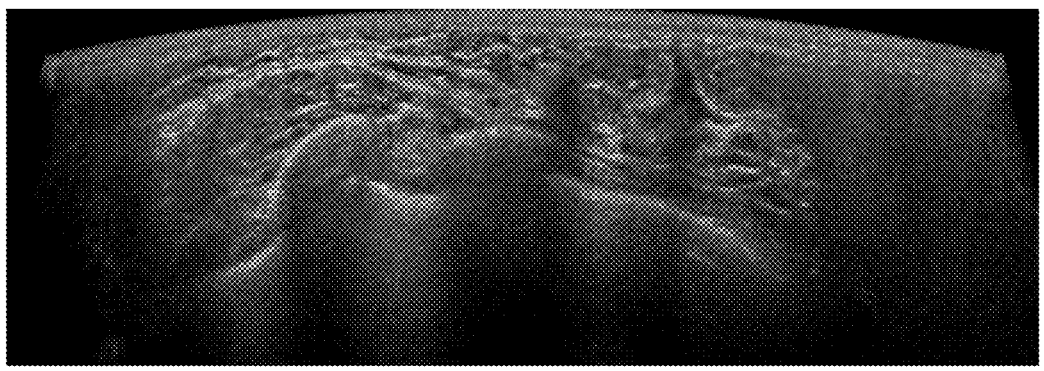
FIG. 10A is an example illustrating another breast ultrasound image according to an embodiment of the invention.
Figure 10B:
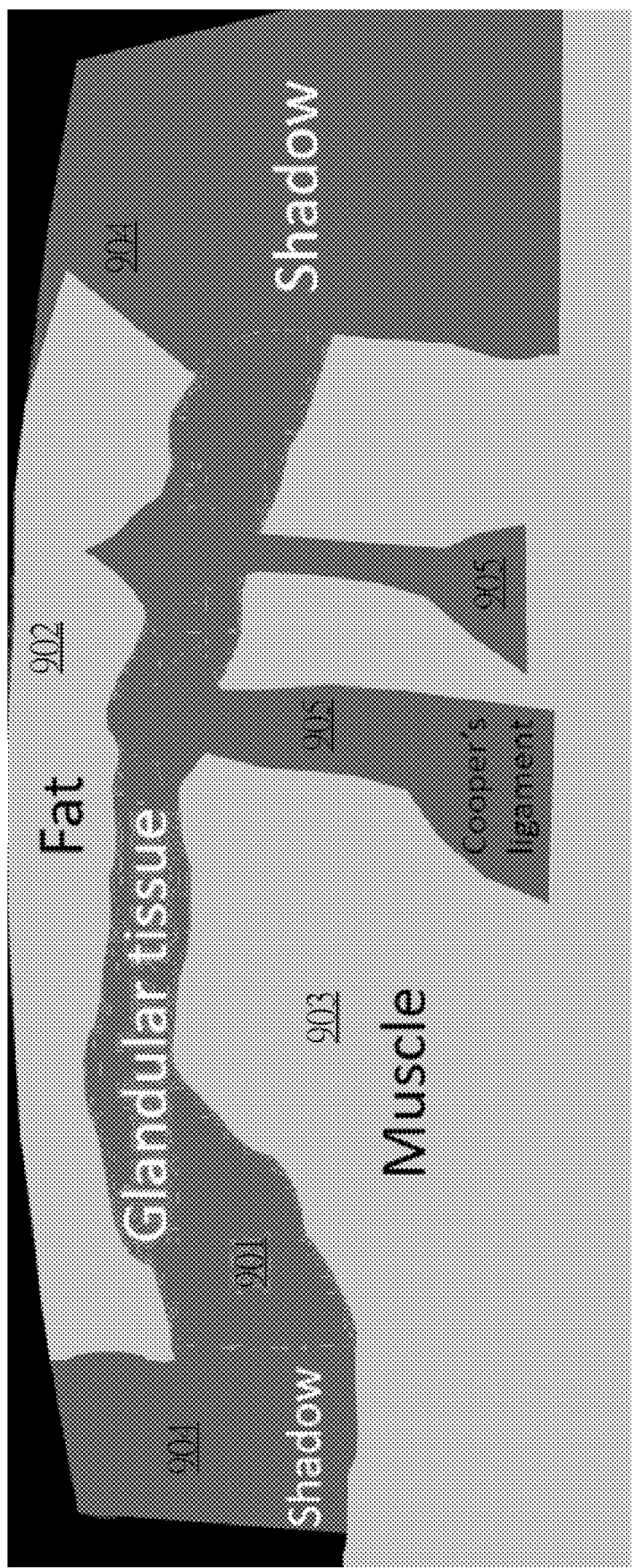
FIG. 10B is a schematic diagram illustrating a tissue segmentation result of FIG. 10A according to an embodiment of the invention.

For another example, FIG. 10A is an example illustrating another breast ultrasound image according to an embodiment of the invention, and FIG. 10B is a schematic diagram illustrating a tissue segmentation result of FIG. 10A according to an embodiment of the invention. Referring to FIGS. 10A and 10B, the tissues may be glandular tissue 901, fat 902, muscle 903, and Copper's ligament 905.

The detection module 124 determines which tissue that the VOI is located. Therefore, the compared result with the tissue segmentation result may be the fact that the VOI is located at a specific tissue or shadow.

The tumor determination module 134 determines the VOI as a false positive according to a compared result between the VOI and the tissue segmentation result (step S870). Specifically, a normal lesion is usually located at the glandular tissue. Therefore, if the compared result is the fact that the VOI is located at another tissue such as fat, muscle, or Cooper's ligament different from the glandular tissue or located at the shadow formed by the probe, the liquid couplant, or the nipple, the tumor determination module 134 determines the VOI as the false positive.

Figures 11, 12:
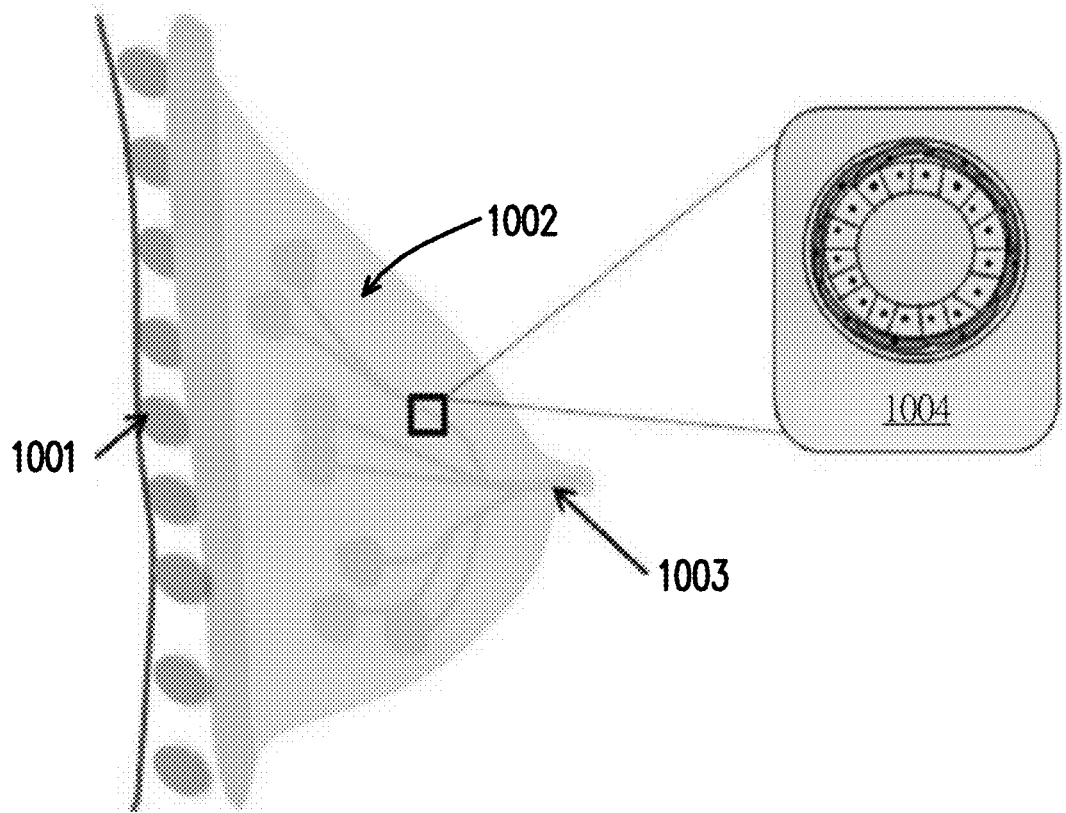
FIG. 11 is a schematic diagram illustrating lactiferous ducts according to an embodiment of the invention.
FIG. 12 is a flowchart illustrating a false positive analysis method for the lactiferous duct according to an embodiment of the invention.

FIG. 11 is a schematic diagram illustrating lactiferous ducts according to an embodiment of the invention. Referring to FIG. 11, it should be noticed that the lactiferous ducts 1004 are located in the glandular tissue 1002 (near to the rib 101), and the lactiferous ducts 1004 may also be the shaded region in the breast ultrasound image.

If the compared result is that the VOI is located at the glandular tissue, the tumor determination module 134 may further determine whether the VOI is the lactiferous ducts.

FIG. 12 is a flowchart illustrating a false positive analysis method for the lactiferous duct according to an embodiment of the invention. Referring to FIG. 12, in step S850, the detection module 124 may further determine that the VOI is located in the glandular tissue of the tissue segmentation result (step S1210). Thus, the compared result comprises the VOI is located at a glandular tissue based on the tissue segmentation result. If the VOI is located in the glandular tissue, the detection module 124 may compare the VOI with the lactiferous duct in the 3D breast model (step S1230).

In one embodiment, the detection module 124 may reconstruct one or more lactiferous ducts in the 3D breast model. Taking FIG. 11 as an example, the lactiferous ducts 1004 are started from the nipple 1003. The detection module 124 may determine the nipple 1003 is the center of these lactiferous ducts 1004 and connect shaded regions from the nipple 1003 through FloodFill algorithm or another connecting related algorithm. It means that the nipple 1003 is the starting point of the lactiferous ducts 1004. If the detection module 124 connects the shaded regions from the nipple toward the outside, the connected shaped regions would form reconstructed lactiferous. The detection module 124 may further determine whether the VOI is located at the reconstructed lactiferous duct.

If the compared result is that the VOI is located at the glandular tissue but not the lactiferous duct, the tumor determination module 134 determines the VOI is a lesion (belonging to true positive). In one embodiment, if the compared result is that the VOI is located at the glandular tissue and the lactiferous duct, the tumor determination module 134 determines the VOI is not the lesion (belonging to false positive).

Figure 13:
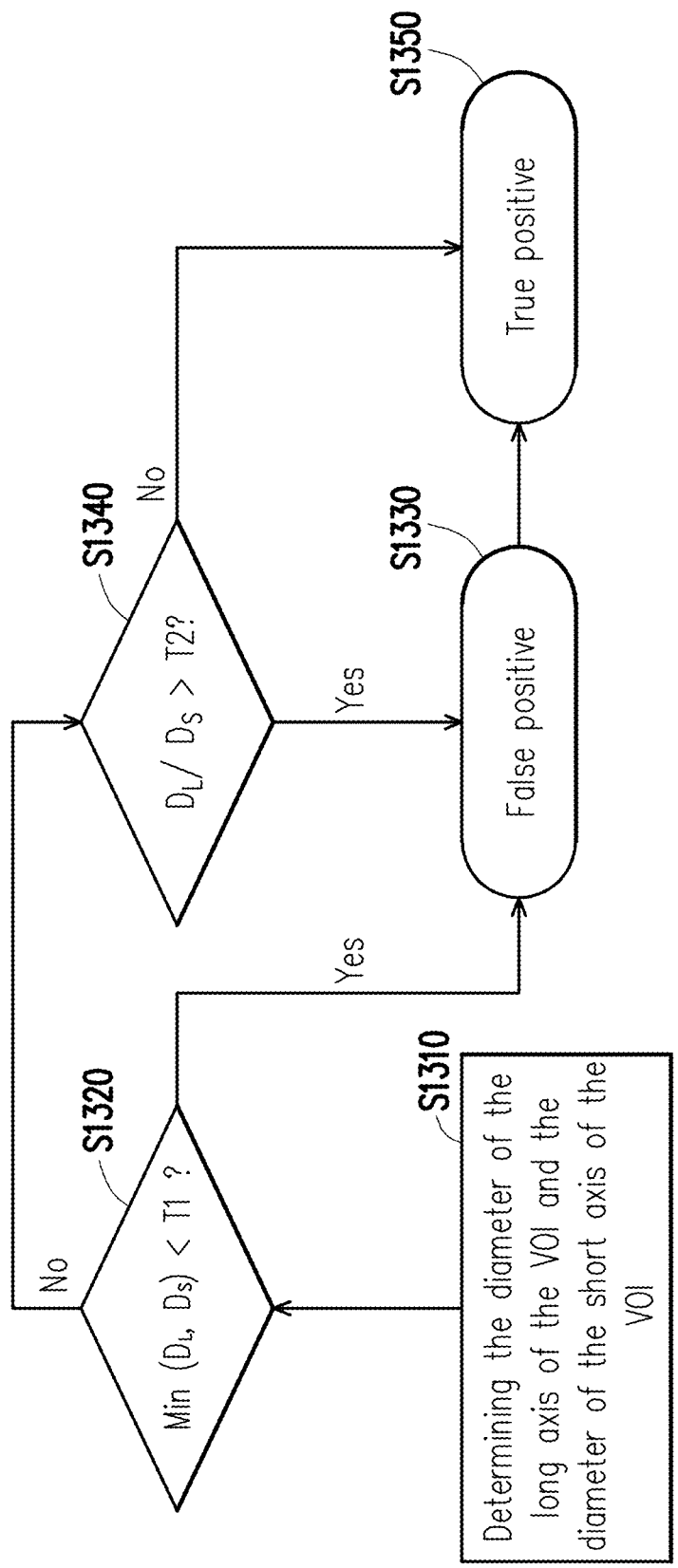
FIG. 13 is a flowchart illustrating a false positive analysis method with reconstructed lactiferous duct according to an embodiment of the invention.

In another embodiment, if the compared result is that the VOI is located at the glandular tissue and the lactiferous duct, the tumor determination module 134 may provide further confirmation of the false positive. FIG. 13 is a flowchart illustrating a false positive analysis method with reconstructed lactiferous duct according to an embodiment of the invention. Referring to FIG. 13, the tumor determination module 134 determines the diameter $D_L$ of the long axis of the VOI and the diameter $D_S$ of the short axis of the VOI by using Feret diameter measurement or another diameter measurement (step S1310). The tumor determination module 134 may determine the VOI as the false positive according to a compared result of the diameter $D_L$ and the diameter $D_S$.

In one embodiment, the compared result of the diameter $D_L$ and the diameter $D_S$ is related to the shortest one of the diameter $D_L$ and the diameter $D_S$. Min (.) means that a selection of the shortest one from the two diameters $D_L$ and $D_S$. The tumor determination module 134 may compare the shortest one (Min ($D_L$, $D_S$)) with a threshold T1 such as 5 nm, 5.5 nm, or 6 nm (step S1320). If the shortest one is less than the threshold T1, the tumor determination module 134 determines the VOI as the false positive (step S1330).

In one embodiment, the compared result of the diameter $D_L$ and the diameter $D_S$ is related to a ratio of diameter $D_L$ and the diameter $D_S$. If the shortest one is not less than the threshold T1, the tumor determination module 134 may compare the ratio of diameter $D_L$ to the diameter $D_S$ ($D_L/D_S$) with a threshold T2 such as 2.5, 2.6, or 2.8 (step S1340). If the ratio of diameter $D_L$ to the diameter $D_S$ is larger than the threshold T2, the tumor determination module 134 determines the VOI as the false positive (step S1330). If the ratio of diameter $D_L$ to the diameter $D_S$ is not larger than the threshold T2, the tumor determination module 134 determines the VOI as the true positive (step S1330).

In one embodiment, the tumor determination module 134 may obtain multiple section view images based on the VOL These section view images correspond to different anatomical planes such as the transverse plane, the coronal plane, and the sagittal plane. The tumor determination module 134 may compare the VOI located on these section view images. In one embodiment, if the VOI exists in all section view images, the tumor determination module 134 determines the VOI as the true positive. If the VOI does not exist in all section view images, the tumor determination module 134 determines the VOI as the false positive.

Figure 14:
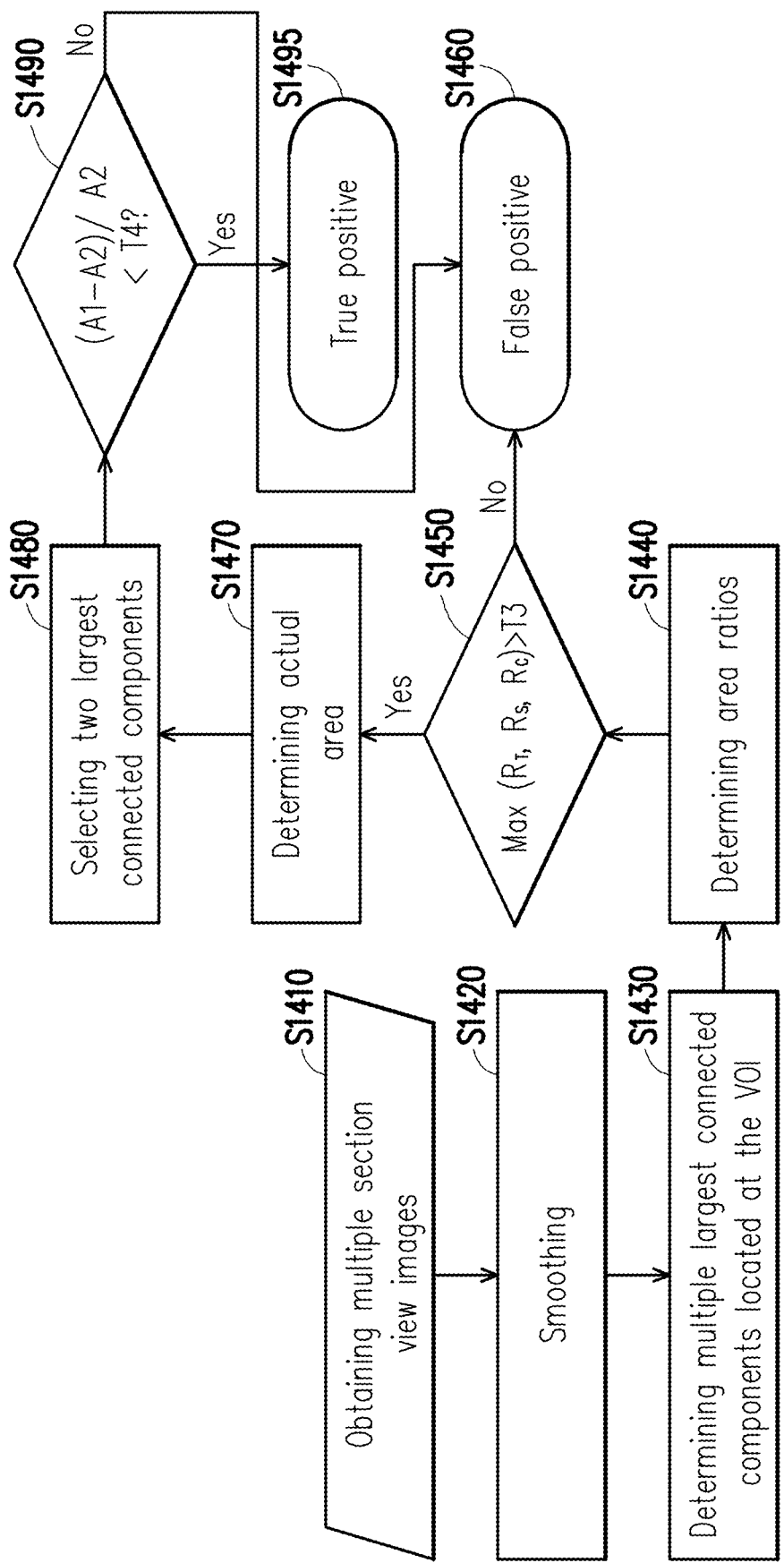
FIG. 14 is a flowchart illustrating a false positive analysis method with multiple section views according to an embodiment of the invention.

FIG. 14 is a flowchart illustrating a false positive analysis method with multiple section views according to an embodiment of the invention. Referring to FIG. 14, in one embodiment, the tumor determination module 134 may obtain multiple section view images (step S1410). For example, three section view images at the transverse plane, the coronal plane, and the sagittal plane are obtained. The tumor determination module 134 may perform smoothing or blur processing on these section view images (step S1420). The tumor determination module 134 may determine multiple largest connected components located at the VOI in the obtained section view images respectively (step S1430). These connected components are connected shaded regions in the ultrasound images and may be the lactiferous ducts. The tumor determination module 134 may determine the VOI as the false positive according to a compared result of these largest connected components.

In one embodiment, the compared result of these largest connected components is related to the largest one of ratios of area sizes of these largest connected components to the VOL The tumor determination module 134 may determine the ratio of area size of each largest connected component to the VOI (step S1440). For example, the ratios of area sizes RT, RS, and RC at the transverse plane, the sagittal plane, and the coronal plane is determined. The tumor determination module 134 may select the largest one of the ratios of area sizes (Max (RT, RS, RC)) and compare with a threshold T3 such as 0.5, 0.6, or 0.55 (step S1450). If the largest one of ratios of area sizes is not larger than the threshold T3, the tumor determination module 134 determines the VOI as the false positive (step S1460). In one embodiment, if the largest one of area ratios is larger than the threshold T3, the tumor determination module 134 determines the VOI as the true positive (step S1495).

In one embodiment, the compared result of these largest connected components is related to a ratio of area size of a difference of two of the largest connected components to one of the largest connected components. The tumor determination module 134 may determine the actual area size of these largest connected components by using spacing or another size measurement (step S1470). For example, the actual area size AT, AS, and AC at the transverse plane, the sagittal plane, and the coronal plane is determined. The tumor determination module 134 may select the two largest connected components with the largest actual area sizes A1 and A2 (step S1480). For example, A1=Max ([AT, AS, AC]), and A2=Max([AT, AS, AC]-A1). It means that the actual area size A1 is the largest one, and the actual area size A2 is the largest one or the second largest one. The tumor determination module 134 may compare the ratio of area size of the difference between the two largest actual area sizes A1 and A2 to the one largest actual area size A2 with threshold T4 such as 0.3, 035, or 0.4 (step S1490). If the ratio of area size ((A1−A2)/A2) is not larger than the threshold T4, the tumor determination module 134 determines the VOI as the false positive (step S1460). If the ratio of area size is larger than the threshold T4, the tumor determination module 134 determines the VOI as the true positive (step S1495).

Figure 15:
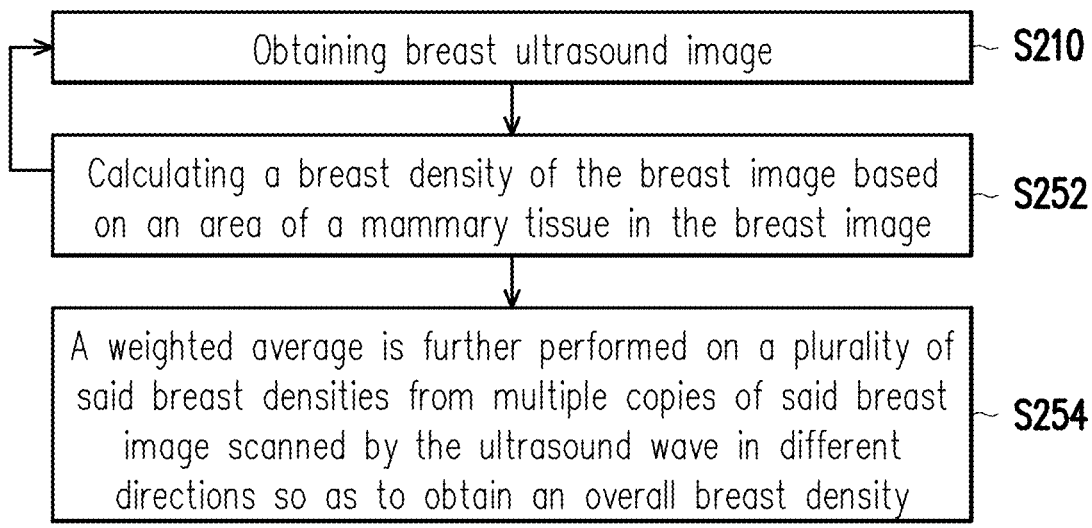
FIG. 15 illustrates a flowchart for obtaining an overall breast density according to an embodiment of the invention.

FIG. 15 illustrates a flowchart for obtaining an overall breast density according to an embodiment of the invention. With reference to FIG. 1 and FIG. 15, after the breast image is obtained by the image input module 122 (step S210), the density analysis module 132 calculates a breast density of the breast image based on an area of a mammary tissue in the breast image (step S252). Specifically, in the present embodiment, the breast image scanned by the ultrasound device has a fixed dimension or resolution. The density analysis module 132 determines a position and an area of the mammary tissue in the breast image by, for example, a trained mammary detection model, and use a dimension of the breast image for calculating a proportion occupied by the mammary tissue as the breast density of the breast image.

In the embodiment described above, when the breast part of the subject is scanned by the ultrasound device, it is required to obtain multiple of the breast images by scanning in different directions. Herein, after calculating the corresponding breast density for each of the breast image, the density analysis module 132 performs a weighted average on the breast densities from all of the breast images so as to further obtain an overall breast density (step S254). The overall breast density includes the breast densities of said multiple of the breast images scanned in various directions, and can therefore be regarded as a substantial breast density of the breast part and served as a reference feature parameter in diagnosis for breast tumor or lesion.

Figure 16:
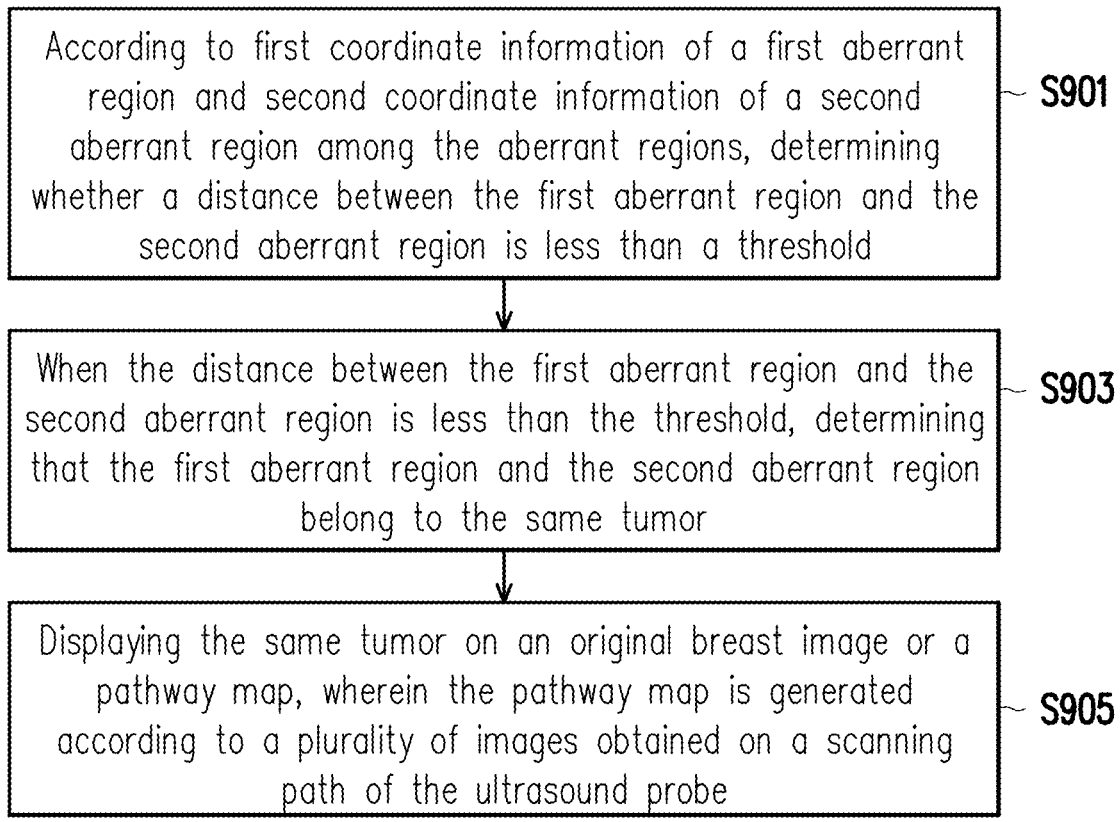
FIG. 16 is a flowchart for determining and displaying multiple aberrant regions as the same tumor according to an embodiment of the invention.

It should be noted that, a plurality of aberrant regions may be acquired from one breast image with the analysis method for breast image described above, and the aberrant regions are possible positions of tumors and masses in the breast part. In an embodiment of the invention, whether the aberrant regions are of the same tumor may be further determined. FIG. 16 is a flowchart for determining and displaying multiple aberrant regions as the same tumor according to an embodiment of the invention. With reference to FIG. 1 and FIG. 16, after acquiring the aberrant region from the region of interest (i.e., step S230 of FIG. 2), the acquisition module 126 can, for example, obtain a plurality of the aberrant regions in the breast image. Then, according to first coordinate information of a first aberrant region and second coordinate information of a second aberrant region among the aberrant regions, whether a distance between the first aberrant region and the second aberrant region is less than a threshold can be determined by the tumor determination module 134 (step S901).

In detail, when the electronic apparatus 100 scans and obtains an original image by using, for example, the magnetic tracker ultrasound scanning system, a coordinate of a reference point may be set and a 3D coordinate information can be simultaneously recorded for each position in the obtained image according to the coordinate of the reference point. After the aberrant regions are acquired by the acquisition module 126, the tumor determination module 134 can obtain the 3D coordinate information of these aberrant regions, and classify the aberrant regions according to the 3D coordinate information so as to determine the aberrant regions closing to one other as the same tumor. In the present exemplary embodiment, when the distance between one aberrant region (e.g., said first aberrant region) and another aberrant region (e.g., said second aberrant region) among the aberrant regions in terms of 3D coordinate is less than the threshold, the tumor determination module 134 can determine that these two aberrant regions belong to the same tumor (step S903). In particular, the invention is not intended to limit a value of the threshold.

In addition, after determining that the aberrant regions belong to the same tumor, the same tumor can be displayed on the obtained original breast image or a pathway map by the display module 136, wherein the pathway map is generated according to a plurality of images obtained on a scanning path of the ultrasound probe (step S905).

Figure 17:
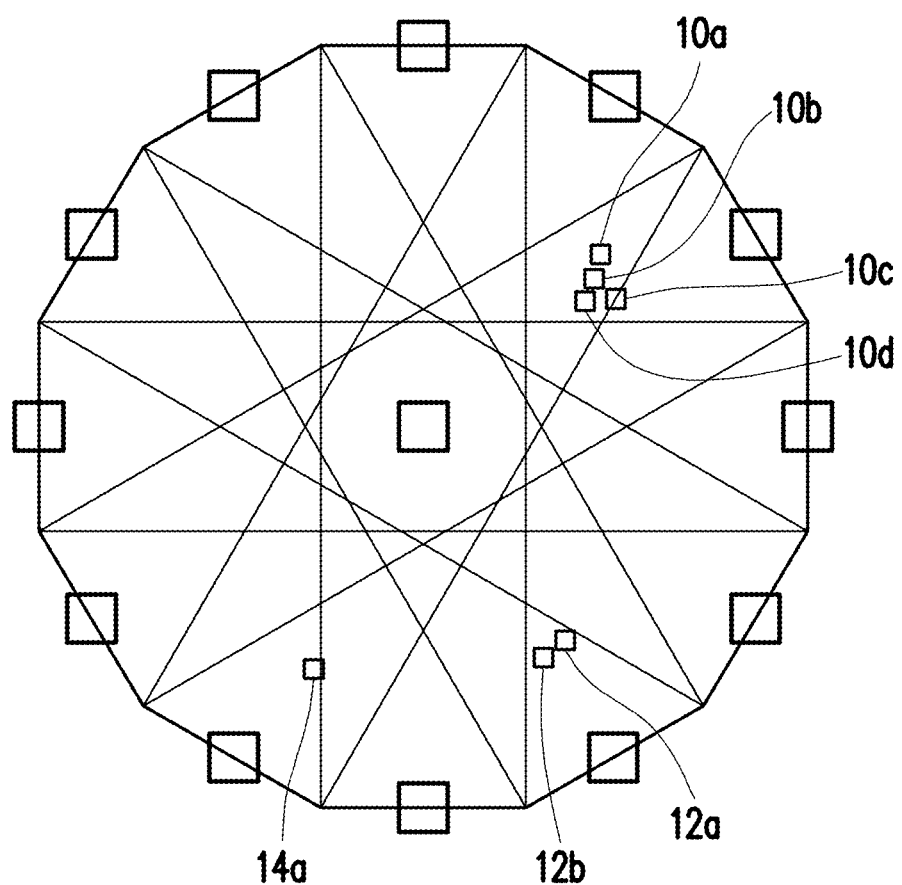
FIG. 17 is a schematic diagram for displaying the tumor onto a pathway map according to an embodiment of the invention.

For instance, in an embodiment of the invention, the breast image is the image obtained by scanning the breast part of the subject with the ultrasound scanning apparatus, the handheld ultrasound scanner, the automated breast ultrasound system or the magnetic tracker ultrasound scanning system. In the process of scanning, one scanning path is formed by a moving trajectory of the device or system for scanning on the breast part of the subject. Meanwhile, the device or system for scanning path and combine the images into one pathway map by the processor 140. When the tumor determination module 134 determines that the aberrant regions belong to the same tumor, the display module 136 can display the same tumor on the pathway map to be outputted through an output device (e.g., a screen) for doctors to conduct an instant diagnosis. In other words, an indication (or a prompt) of the tumor may be provided or outputted through the output device immediately (i.e., in real-time) in the process of scanning. For example, FIG. 17 is a schematic diagram for displaying the tumor onto a pathway map according to an embodiment of the invention. With reference to FIG. 17, the device or system for scanning can acquire multiple images from the breast part of the subject along a scanning path, so the processor 140 can then combine the images into one pathway map as shown in FIG. 17. Meanwhile, the pathway map in FIG. 17 can also display an aberrant region 10a, an aberrant region 10b, an aberrant region 10c, an aberrant region 10d, an aberrant region 12a, an aberrant region 12b and an aberrant region 14a obtained using the method of the invention. In particular, the aberrant region 10a, the aberrant region 10b, the aberrant region 10c and the aberrant region 10d are determined as the same tumor by the tumor determination module 134, and displayed in the pathway map with the same color (e.g., red) by the display module 136. Similarly, the aberrant region 12a and the aberrant region 12b are determined as the same tumor by the tumor determination module 134, and displayed in the pathway map with the same color (e.g., blue) by the display module 136. Specifically, the aberrant region 14a is determined as one independent tumor by the tumor determination module 134, and displayed in the pathway map with one single color (e.g., purple) by the display module 136.

Nonetheless, in an exemplary embodiment, the aberrant region 10a, the aberrant region 10b, the aberrant region 10c and the aberrant region 10d determined as the same tumor may also be displayed superimposingly on the original breast image obtained through the ultrasound wave with the same color (e.g., red) by the display module 136. Similarly, the aberrant region 12a and the aberrant region 12b determined as the same tumor may also be displayed on the original breast image obtained through the ultrasound device with the same color (e.g., blue) by the display module 136. In addition, the aberrant region 14a determined as one independent tumor may also be displayed on the original breast image obtained through the ultrasound wave with one single color (e.g., purple) by the display module 136.

In summary, according to the analysis method for breast image and the electronic apparatus using the same as provided in the embodiments of the invention, the region of interest including the aberrant region is obtained from the breast image by applying the detection model based on the rectangular features of the breast image such that the aberrant region can be acquired from the region of interest. With respect to the aberrant region, the feature parameters can be further extracted for the property analysis, and whether multiple aberrant regions belong to the same tumor can also be determined and correspondingly displayed. As a result, the analysis method and the electronic apparatus using the same can be used to identify the aberrant region with the aberrant symptom while providing the related property analysis. On the other hand, the analysis can be completed rapidly, promptly and effectively even in the case of dealing with a massive number of the breast images.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An analysis method for breast ultrasound images, comprising:
obtaining at least one breast ultrasound image, wherein the at least one breast ultrasound image is used for forming a three dimensional (3D) breast model;
obtaining a volume of interest (VOI) as a suspicious area in the at least one breast ultrasound image by applying a detection model on the 3D breast model, wherein the detection model is trained by a machine learning algorithm;
segmenting the at least one breast ultrasound image into a plurality of tissues, to obtain a tissue segmentation result, wherein the tissue segmentation result comprises the plurality of tissues in the 3D breast model;
determining a type of a target tissue of the plurality of tissue where the VOI is located with the tissue segmentation result;
determining the VOI as a false positive according to the target tissue where the VOI is located, wherein the target tissue where the VOI is located is a glandular tissue based on the tissue segmentation result, and determining the VOI as the false positive according to the target comprises:
determining whether the VOI located in the glandular tissue is further located in a lactiferous duct based on the tissue segmentation result;

in response to the VOI being located in the glandular tissue but not located in the lactiferous duct, determining the VOI as not the false positive; and in response to the VOI being located in both the glandular tissue and the lactiferous duct, determining the VOI as the false positive; and removing the VOI belonging to the false positive from the suspicious area.

2. The analysis method according to claim 1, wherein determining whether the VOI located in the glandular tissue is further located in the lactiferous duct based on the tissue segmentation result comprises:

reconstructing the lactiferous duct in the 3D breast model, wherein the lactiferous duct is started from a nipple; and determining whether the VOI is located at a reconstructed lactiferous duct.

3. The analysis method according to claim 2, wherein reconstructing the lactiferous duct in the 3D breast model comprises:

connecting a plurality of shaded regions on the nipple, wherein the nipple is a center of a plurality of the lactiferous ducts, and the reconstructed lactiferous duct is formed by a plurality of connected shaped regions.

4. The analysis method according to claim 2, wherein determining the VOI as the false positive comprises:

in response to determining that the VOI is located at the reconstructed lactiferous duct, determining a first diameter of a long axis of the VOI and a second diameter of a short axis of the VOI; and providing a confirmation that the VOI is the false positive according to a compared result of the first diameter and the second diameter.

5. The analysis method according to claim 4, wherein the compared result of the first diameter and the second diameter is related to the shortest one of the first diameter and the second diameter or a ratio of the first diameter to the second diameter.

6. The analysis method according to claim 1, wherein comparing the VOI with the lactiferous duct in the 3D breast model comprises:

obtaining a plurality of section view images based on the VOI, wherein the plurality of section view images correspond to different anatomical planes; and comparing the VOI located on the plurality of section view images.

7. The analysis method according to claim 6, wherein determining the VOI as the false positive comprises:

determining a plurality of largest connected components located at the VOI respectively from the plurality of section view images; and providing a confirmation that the VOI is the false positive according to a compared result of the plurality of largest connected components.

8. The analysis method according to claim 7, wherein the compared result of the plurality of largest connected components is related to the largest one of ratios of area sizes of the plurality of largest connected components to the VOI.

9. The analysis method according to claim 7, wherein the compared result of the plurality of largest connected components is related to a ratio of area size of a difference of two of the largest connected components to one of the largest connected components.

10. The analysis method according to claim 1, wherein the compared result comprises the VOI is located at one of fat muscle, shadow, and Cooper's ligament based on the tissue segmentation result.

11. An electronic apparatus, adapted for analyzing ultrasound breast images, the electronic apparatus comprising:

a memory, configured to store a program code;

a processor, coupled to the memory, and configured to access and execute the program code stored by the memory to perform:

obtaining at least one breast ultrasound image, wherein the at least one breast ultrasound image is used for forming a three dimensional (3D) breast model;

obtaining a volume of interest (VOI) as a suspicious area in the at least one breast ultrasound image by applying a detection model on the 3D breast model, wherein the detection model is trained by a machine learning algorithm;

segmenting the at least one breast ultrasound image into a plurality of tissues, to obtain a tissue segmentation result, wherein the tissue segmentation result comprises the plurality of tissues in the 3D breast model;

determining a type of a target tissue of the plurality of tissue where the VOI is located with the tissue segmentation result;

determining the VOI as a false positive according to the target tissue where the VOI is located, wherein the target tissue where the VOI is located is a glandular tissue based on the tissue segmentation result, and the processor is further configured for:

determining whether the VOI located in the glandular tissue is further located in a lactiferous duct based on the tissue segmentation result;

in response to the VOI being located in the glandular tissue but not located in the lactiferous duct, determining the VOI as not the false positive; and in response to the VOI being located in both the glandular tissue and the lactiferous duct, determining the VOI as the false positive; and removing the VOI belonging to the false positive from the suspicious area.

12. The electronic apparatus according to claim 11, wherein the processor is further configured for:

reconstructing the lactiferous duct in the 3D breast model, wherein the lactiferous duct is started from a nipple; and determining whether the VOI is located at a reconstructed lactiferous duct.

13. The electronic apparatus according to claim 12, wherein the processor is further configured for:

connecting a plurality of shaded regions on the nipple, wherein the nipple is a center of a plurality of the lactiferous ducts, and the reconstructed lactiferous duct is formed by a plurality of connected shaped regions.

14. The electronic apparatus according to claim 12, wherein the processor is further configured for:

in response to determining that the VOI is located at the reconstructed lactiferous duct, determining a first diameter of a long axis of the VOI and a second diameter of a short axis of the VOI; and providing a confirmation that the VOI is the false positive according to a compared result of the first diameter and the second diameter.

15. The electronic apparatus according to claim 14, wherein the compared result of the first diameter and the second diameter is related to the shortest one of the first diameter and the second diameter or a ratio of the first diameter to the second diameter.

16. The electronic apparatus according to claim 11, wherein the processor is further configured for:

obtaining a plurality of section view images based on the VOI, wherein the plurality of section view images correspond to different anatomical planes; and comparing the VOI located on the plurality of section view images.

17. The electronic apparatus according to claim 16, wherein the processor is further configured for:

determining a plurality of largest connected components located at the VOI respectively from the plurality of section view images; and providing a confirmation that the VOI is the false positive according to a compared result of the plurality of largest connected components.

18. The electronic apparatus according to claim 17, wherein the compared result of the plurality of largest connected components is related to the largest one of ratios of area sizes of the plurality of largest connected components to the VOI.

19. The electronic apparatus according to claim 17, wherein the compared result of the plurality of largest connected components is related to a ratio of area size of a difference of two of the largest connected components to one of the largest connected components.

20. The electronic apparatus according to claim 11, wherein the compared result comprises the VOI is located at one of fat muscle, shadow, and Cooper's ligament based on the tissue segmentation result.

\* \* \* \* \*